United States Patent [19]

Drabek et al.

[11] 4,150,160
[45] Apr. 17, 1979

[54] PESTICIDAL CARBIMIDOCARBONYLPHENYLFOR-MAMIDINES

[75] Inventors: Jozef Drabek, Oberwil; Ernst Beriger, Allschwil, both of Switzerland; Manfred Boger, Weil am Rhein, Fed. Rep. of Germany

[73] Assignee: Ciba-Geigy Corporation, Ardsley, N.Y.

[21] Appl. No.: 867,651

[22] Filed: Jan. 6, 1978

[30] Foreign Application Priority Data

Jan. 12, 1977 [CH] Switzerland .......................... 340/77
Dec. 19, 1977 [CH] Switzerland ....................... 15613/77

[51] Int. Cl.² .................. A01N 9/20; C07C 127/00
[52] U.S. Cl. .................. 424/322; 260/465 D; 260/553 E; 424/304
[58] Field of Search .............. 424/322; 260/553 E

[56] References Cited

U.S. PATENT DOCUMENTS

| | | | |
|---|---|---|---|
| 3,898,277 | 8/1975 | Duerr et al. | 260/552 R |
| 4,005,223 | 1/1977 | Sirrenberg et al. | 424/322 |
| 4,008,330 | 2/1977 | Yamamoto et al. | 424/322 |

Primary Examiner—Allen J. Robinson
Attorney, Agent, or Firm—Frederick H. Rabin

[57] ABSTRACT

Carbimidocarbonylphenylformamidines of the formula

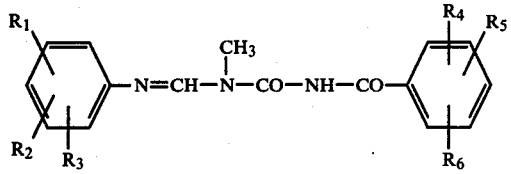

wherein each of $R_1$ to $R_6$ represents hydrogen, halogen, $C_1-C_4$ alkyl, $C_1-C_4$ alkoxy, trifluoromethyl or cyano, a process for their production and their use in pest control.

15 Claims, No Drawings

PESTICIDAL CARBIMIDOCARBONYLPHENYLFORMAMIDINES

The present invention relates to carbimidocarbonylphenylformamidines, to a process for their manufacture and to their use in pest control.

The carbimidocarbonylphenylformamidines have the formula

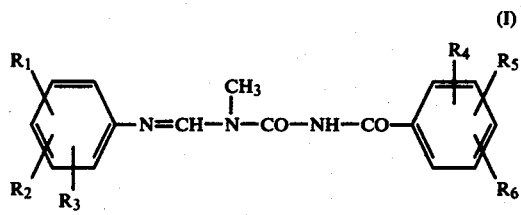
(I)

wherein each of $R_1$ to $R_6$ represents hydrogen, halogen, $C_1$-$C_4$alkyl, $C_1$-$C_4$alkoxy, trifluoromethyl or cyano.

By halogen is meant fluorine, chlorine, bromine or iodine, especially chlorine or bromine. The alkyl and alkoxy groups represented by $R_1$ to $R_6$ can be straight-chain or branched. Examples of such groups include: methyl, methoxy, ethyl, ethoxy, propyl, butoxy, propoxy, isopropyl, isopropoxy, n-butyl, n-butoxy, isobutyl, sec-butyl and tert-butyl.

Preferred compounds on account of their action are those of the formula I wherein each of $R_1$, $R_2$ and $R_3$ represents hydrogen, chlorine, bromine or methyl, and each of $R_4$, $R_5$ and $R_6$ represents hydrogen, fluorine, chlorine or methyl.

The compounds of the formula I can be prepared by known methods, for example (a) by reacting a compound of the formula

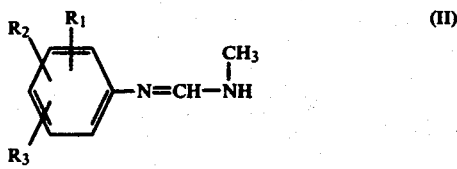
(II)

with a compound of the formula

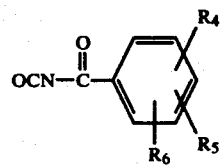
(III)

or (b) by reacting a compound of the formula

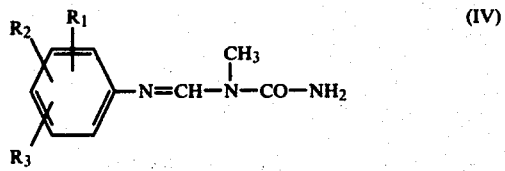
(IV)

with a compound of the formula

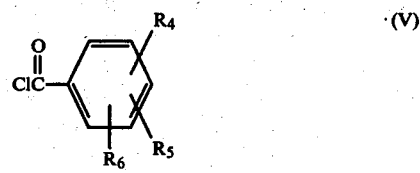
(V)

optionally in the presence of an acid acceptor.

In the above formulae (II) to (V), $R_1$ to $R_6$ are as defined in formula (I). Suitable acid acceptors for process (b) are in particular amines, such as trialkylamine and pyridine, also hydroxides, oxides, carbonates and bicarbonates of alkali metals and alkaline earth metals, as well as alkali metal alcoholates, for example potassium tertbutylate and sodium methylate. Processes (a) and (b) are carried out at a reaction temperature between $-10°$ C. and $+100°$ C., usually between $20°$ and $80°$ C., under normal or elevated pressure and preferably in an inert solvent or diluent. Examples of suitable solvents or diluents are: ethers and ethereal compounds, such as diethyl ether, dipropyl ether, dioxane, dimethoxyethane and tetrahydrofurane; amides, such as N,N-dialkylated carboxamides; aliphatic, aromatic and halogenated hydrocarbons, in particular benzene, toluene, xylene, chloroform and chlorobenzene; nitriles, such as acetonitrile; dimethyl sulphoxide; ketones, such as acetone and methyl ethyl ketone.

The starting materials of the formulae (II) to (V) are known or they can be prepared by methods analogous to known ones.

The compounds of the formula I are suitable for controlling a variety of animal and plant pests. They possess nematicidal properties and can be used for example to control phytopathogenic nematodes. They are also suitable for controlling viruses, bacteria and phytopathogenic fungi. In particular, the compounds of the formula I are suitable for controlling insects, phytopathogenic mites and ticks, for example of the orders: Lepidoptera, Coleoptera, Homoptera, Heteroptera, Diptera, Acarina, Thysanoptera, Orthoptera, Anoplura, Siphonaptera, Mallophaga, Thysanura, Isoptera, Procoptera and Hymenoptera.

In particular, the compounds of the formula I are suitable for controlling insects which are harmful to plants, especially insects which damage plants by eating, in ornamentals and crops of useful plants, especially in cotton plantations (e.g. *Spodoptera littoralis* and *Heliothis virescens*) and in vegetable crops (for example *Leptinotarsa decemlineata* and *Myzus persicae*).

The active compounds of the formula I also have a very good action against flies, for example *Musca domestica* and mosquito larvae.

The insecticidal and/or acaricidal action can be substantially broadened and adapted to prevailing circumstances by addition of other insecticides and/or acaricides. Examples of suitable additives include: organic phosphorus compounds, nitrophenols and derivatives thereof, formamidines, ureas, pyrethroids, carbamates, and chlorinated hydrocarbons.

Compounds of the formula I are also combined with particular advantage with substances which exert a potentiating effect. Examples of such compounds include: piperonyl butoxide, propynyl ether, propynyl oximes, propynyl carbamates and propynyl phosphonates, 2-(3,4-methylenedioxyphenoxy)-3,6,9-trioxaundecane, S,S,S-tributylphosphorotrithioate.

The compounds of the formula I may be used as pure active substance or together with suitable carriers and/or additives. Suitable carriers and additives can be solid or liquid and correspond to the substances conventionally used in the art of formulation, for example natural or regenerated substances, solvents, dispersants, wetting agents, tackifiers, thickeners, binders and/or fertilisers.

For application, the compounds of the formula I may be processed to dusts, emulsifiable concentrates, granules, dispersions, sprays, to solutions, or suspensions, in the conventional formulation which is commonly employed in application technology. In addition, cattle dips and spray races, in which aqueous preparations are used, may also be mentioned.

The compositions of the present invention are prepared in known manner by homogeneously mixing and/or grinding active substances of the formula I with the suitable carriers, with or without the addition of dispersants or solvents which are inert to the active substances.

The compounds of the formula I may be processed to the following formulations:

Dusts, tracking powders and granules (coated granules, impregnated granules and homogeneous granules).

Liquid formulations:
(a) water-dispersible active substance concentrates: wettable powders, pastes and emulsions;
(b) solutions.

The content of active substance in the above described compositions is between 0.1% and 95%.

The compounds (active substances) of the formula I can, for example, be formulated as follows (throughout the present specification all parts and percentages are by weight):

Dusts

The following substances are used to manufacture (a) a 5% and (b) a 2% dust:

(a)
5 parts of active substance,
95 parts of talc;

(b)
2 parts of active substance,
1 part of highly disperse silicic acid,
97 parts of talc.

The active substances are mixed with the carriers and ground.

Granules

The following substances are used to produce 5% granules:
5 parts of active substance,
0.25 parts of epichlorohydrin,
0.25 parts of cetyl polyglycol ether,
3.50 parts of polyethylene glycol,
91 parts of kaolin (particle size 0.3–0.8 mm).

The active substance is mixed with epichlorohydrin and the mixture is dissolved in 6 parts of acetone; the polyethylene glycol and cetyl polyglycol ether are then added. The resultant solution is sprayed on kaolin, and the acetone is subsequently evaporated in vacuo.

Wettable Powders

The following constituents are used for the preparation of (a) a 40%, (b) and (c) a 25%, and (d) a 10% wettable powder:

(a)
40 parts of active substance,
5 parts of sodium ligninsulphonate,
1 part of sodium dibutylnaphthalenesulphonate,
54 parts of silicic acid.

(b)
25 parts of active substance,
4.5 parts of calcium ligninsulphonate,
1.9 parts of Champagne chalk/hydroxyethyl cellulose mixture (1:1),
1.5 parts of sodium dibutylnaphthalenesulphonate,
19.5 parts of silicic acid,
19.5 parts of Champagne chalk,
28.1 parts of kaolin, (c)
25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselguhr,
46 parts of kaolin;

(d)
10 parts of active substance,
3 parts of a mixture of the sodium salts of saturated fatty alcohol sulphates,
5 parts of naphthalenesulphonic acid/formaldehyde condensate,
82 parts of kaolin.

The active substances are homogeneously mixed with the additives in suitable mixers and the mixture is then ground in appropriate mills and rollers. Wettable powders are obtained which can be diluted with water to give suspensions of the desired concentration.

Emulsifiable Concentrates

The following substances are used to produce (a) a 10%, (b) a 25% and (c) a 50% emulsifiable concentrate:

(a)
10 parts of active substance,
3.4 parts of epoxidised vegetable oil,
3.4 parts of a combination emulsifier consisting of fatty alcohol polyglycol ether and alkylarylsulphonate calcium salt,
40 parts of dimethyl formamide,
43.2 parts of xylene;

(b)
25 parts of active substance,
2.5 parts of epoxidised vegetable oil,
10 parts of alkylarylsulphonate/fatty alcohol polyglycol ether mixture,
5 parts of dimethyl formamide,
57.5 parts of xylene;

(c)
50 parts of active substance,
4.2 parts of tributylphenol-polyglycol ether,
5.8 parts of calcium dodecylbenzenesulphonate,
20 parts of cyclohexanene,
20 parts of xylene.

By diluting these concentrates with water it is possible to obtain emulsions of the required concentration.

Sprays

The following ingredients are used to prepare (a) a 5% spray, and (b) a 95% spray:

(a)
5 parts of active substance,
1 part of epichlorohydrin,
94 parts of ligroin (boiling range 160°–190° C.);

(b)
95 parts of active substance,
5 parts of epichlorohydrin.

The invention is further illustrated by the following Examples.

EXAMPLE 1

Preparation of N-2-methyl-4-chlorophenyl-N'-methyl-N'-carbamidocarbonyl-2,6-dichlorophenylformamidine 11.3 g of N-2-methyl-4-chlorophenyl-N'-methylformamidine are added dropwise at 20° to 35° C. to a solution of 18.3 g of carbonyl-2,6-dichlorophenylisocyanate in 50 ml of methylene chloride and the solution is then stirred for 3 hours at room temperature. The precipitated crystals are collected by filtration, washed on the suction filter with methylene chloride and dried in vacuo, affording the compound of the formula

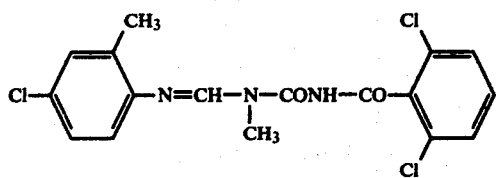

as colourless crystals with a melting point of 163°–166° C. The following compounds are also prepared in analogous manner:

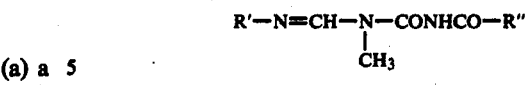

-continued $$R'-N=CH-N(CH_3)-CONHCO-R''$$

| R' | R'' | Physical data |
|---|---|---|
| 3,4-dichlorophenyl (Cl, Cl-) | 2,6-difluorophenyl (F, F-) | m.p.: 148°–150° C. |
| 4-chlorophenyl (Cl-) | 2,6-difluorophenyl (F, F-) | m.p.: 123°–127° C. |
| 3,5-bis(trifluoromethyl)phenyl (CF$_3$, CF$_3$-) | 2,6-difluorophenyl (F, F-) | m.p.: 60°–63° C. |

EXAMPLE 2

(A) Insecticidal Stomach Poison Action

Cotton plants were sprayed with a 0.05% aqueous emulsion of active substance (obtained from a 10% emulsifiable concentrate). After the spray coating had dried, the cotton plants were populated with *Spodoptera littoralis* and *Heliothis virescens* in the L$_3$-stage. The text was carried out at 24° C. and 60% relative humidity.

In this text, the compounds of Example 1 exhibited a good insecticidal stomach poison action against Spodoptera and Heliothis larvae.

(B) Systemic Insecticidal Action

To determine the systemic action, bean plants (*Vicia fabia*) which had grown roots were put into a 0.01% aqueous solution of active substance (obtained from a 10% emulsifiable concentrate). Twenty four hours later, the parts of the plants above the soil were populated with aphids (*Aphis fabae*). By means of a special device the aphids were protected from any possible contact with the test substance either directly or via the gas phase. The test was carried out at 24° C. and 70% relative humidity.

In this test, the compounds of Example 1 exhibited a systemic insecticidal action against *Aphis fabae*.

EXAMPLE 3

Action against *Chilo suppressalis*

Rice seedlings of the variety Caloro were transplanted into plastic pots (6 plants per pot) having a diameter of 17 cm at the top and reared to a height of about 60 cm. Infestation with *Chilo suppressalis* larvae (L$_1$-stage, 3 to 4 mm in length) took place two days after the addition of active substance in granule form (rate of application: 8 kg of active ingredient per hectare) to the paddy water. Evaluation of the insecticidal action was made 10 days after addition of the granules.

In this test, the compounds of Example 1 acted against *Chilo suppressalis*.

EXAMPLE 4

Acaricidal Action

Twelve hours before the test for acaricidal action, Phaseolus vulgaris plants were populated with an infested piece of leaf from a mass culture of *Tetranychus urticae*. The mobile stages which had migrated to the plants were sprayed with the emulsified test preparations from a chromatography atomiser in such a way that the spray broth did not run off. The number of living and dead larvae, adults and eggs was evaluated under a stereoscopic microscope after 2 and 7 days and the result expressed in percentage values. During the test run, the plants stood in greenhouse compartments at 25° C.

In this test, the compounds of Example 1 acted against adults, larvae and eggs of *Tetranychus urticae*.

EXAMPLE 5

Action against Soil Nematodes

To test the action against soil nematodes, the active substances were homogeneously mixed with soil infected with root gall nematodes (*Meloidgyne arenaria*). Young tomato plants were planted in the treated soil in one test run immediately afterwards and then 8 days later further tomatoes were sown in a second test run.

The nematicidal action was evaluated by counting the number of galls present on the roots 28 days after planting and sowing respectively. In this test, the active compounds of Example 1 exhibited a good action against *Meloidogyne arenaria*.

EXAMPLE 6

Action on Ticks (A) *Rhipicephalus bursa*

Five adult ticks and 50 tick larvae were counted into each of a number of test tubes and immersed for 1 to 2 minutes in 2 ml of an aqueous emulsion containing a concentration of 100, 10, 1 or 0.1 ppm of test substance. Each test tube was then sealed with a cotton-wool plug and placed on its head to enable the cotton wool to absorb the active substance emulsion. Evaluation of the action against adults was made after 2 weeks and of that against larvae after 2 days. Each test was repeated twice.

(B) *Boophilus microplus* (larvae)

Test were carried out with 20 OP-sensitive and 20 OP-resistant larvae using aqueous emulsions similar to those used in Test A. (The resistance refers to the tolerance towards diazinone). The compounds of Example 1 acted in these tests against adults and larvae of *Rhipicephalus bursa* and OP-sensitive and OP-resistant larvae of *Boophilus microplus*.

EXAMPLE 7

Action against *Erysiphe graminis* on *Hordeum vulgare*

Barley plants about 8 cm in height were sprayed with a spray broth (0.05% of active ingredient) prepared from a wettable powder of the active compound. 48 Hours later, the treated plants were dusted with conidia of the fungus. The infected barley plants were stood in a greenhouse at about 22° C. and the fungus attack was evaluated after 10 days. In this test, the compounds of Example 1 acted against *Erysiphe graminis*.

What is claimed is:

1. A compound of the formula

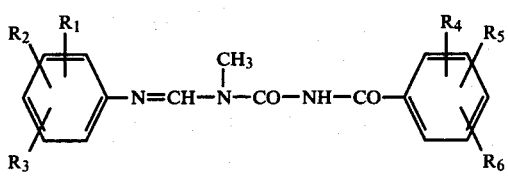

wherein each of $R_1$ to $R_6$ represents hydrogen, halogen, $C_1$-$C_4$alkyl, $C_1$-$C_4$alkoxy or, trifluoromethyl.

2. A compound according to claim 1 wherein each of $R_1$, $R_2$ and $R_3$ represents hydrogen, chlorine, bromine or methyl, and each of $R_4$, $R_5$ and $R_6$ represents hydrogen, fluorine, chlorine or methyl.

3. The compound according to claim 2 of the formula

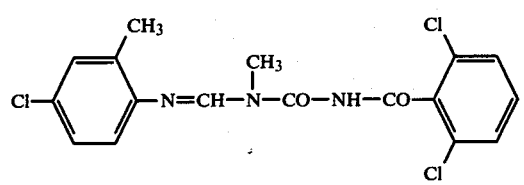

4. The compound according to claim 2 of the formula

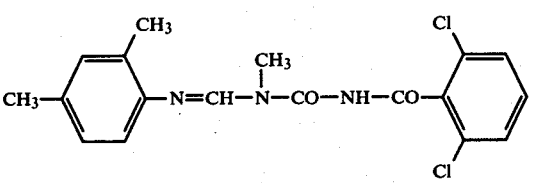

5. The compound according to claim 2 of the formula

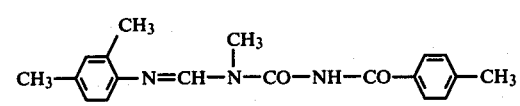

6. The compound according to claim 2 of the formula

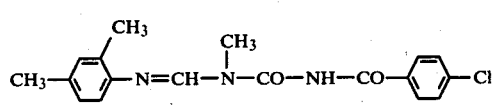

7. The compound according to claim 2 of the formula

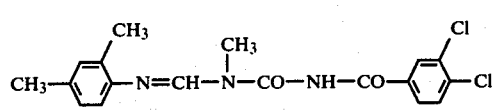

8. The compound according to claim 2 of the formula

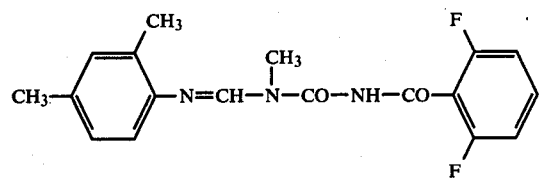

9. The compound according to claim 2 of the formula

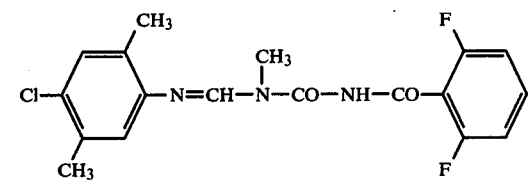

10. The compound according to claim 2 of the formula

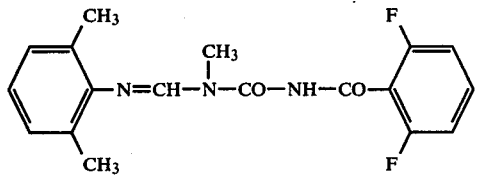

11. The compound according to claim 2 of the formula

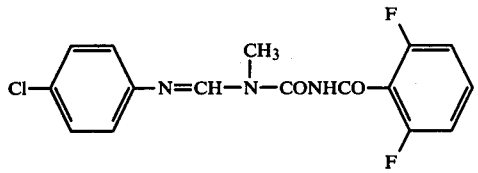

12. A pesticidal composition which contains as active component an insecticidally or acaricidally effective amount of a compound according to claim 1 and a carrier.

13. A method for combatting insects and acarids which comprises applying thereto an insecticidally or acarocidally effective amount of a compound according to claim 1.

14. A method for combatting insects and acarids which comprises applying thereto an insecticidally or acarocidally effective amount of a compound according to claim 2.

15. A compound according to claim 1 of the formula

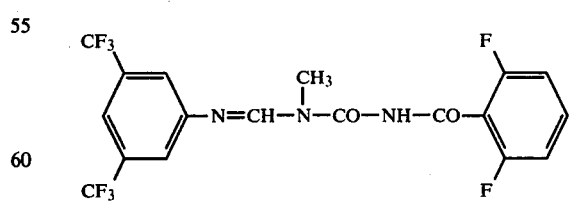

* * * * *